United States Patent
Warner et al.

(10) Patent No.: US 7,048,918 B2
(45) Date of Patent: May 23, 2006

(54) INSECT BAIT

(75) Inventors: Jack Richard Warner, Boca Raton, FL (US); Rudolf H. Scheffrahn, Plantation, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 56 days.

(21) Appl. No.: 10/635,310

(22) Filed: Aug. 6, 2003

(65) Prior Publication Data

US 2004/0057976 A1    Mar. 25, 2004

Related U.S. Application Data

(60) Provisional application No. 60/401,456, filed on Aug. 6, 2002.

(51) Int. Cl.
*A01N 37/44* (2006.01)
*A01N 59/14* (2006.01)
*A01N 43/04* (2006.01)
*A01M 1/02* (2006.01)

(52) U.S. Cl. ............... 424/84; 424/660; 514/23; 514/53; 514/54; 514/400; 514/419; 514/423; 514/556; 514/557; 514/561; 514/562; 514/563; 514/564; 514/565; 514/567; 514/568

(58) Field of Classification Search ............... 424/84, 424/660; 514/23, 53, 54, 400, 419, 423, 514/556–557, 561–565, 567–568
See application file for complete search history.

(56) References Cited

U.S. PATENT DOCUMENTS

| | | | |
|---|---|---|---|
| 3,972,993 A | 8/1976 | Kobayashi et al. | |
| 4,470,979 A | 9/1984 | Van Gestel | |
| 5,850,707 A | 12/1998 | Fell et al. | |
| 5,874,097 A | 2/1999 | Henderson et al. | |
| 6,153,181 A | 11/2000 | Nelson et al. | |
| 6,223,465 B1 * | 5/2001 | Soller et al. | 43/131 |
| 2001/0033855 A1 | 10/2001 | Barcay et al. | |

FOREIGN PATENT DOCUMENTS

| | | | |
|---|---|---|---|
| JP | 52-57325 | * | 5/1977 |
| JP | 09-301806 A1 | | 11/1997 |

OTHER PUBLICATIONS

Nakamura, A., "Organic acids, free amino acids and sugars compositions in ume (Prunus mume) extract . . . " Journal of Japanese Society of Nutrition and Food Science, 1995, vol. 48(3), pp. 232-235.*

Derwent Abstract 1977-44395Y, abstracting JP 52-057325 (May 1977).*

The Merck Index, Merck & Co., Inc., Whitehouse Station, NJ, 12th ed., p. 1471, entry # 8725.*

* cited by examiner

*Primary Examiner*—John Pak
(74) *Attorney, Agent, or Firm*—Akerman Senterfitt; Gregory A. Nelson; Mark A. Buese

(57) ABSTRACT

Disclosed are insect baits for attracting insects such as ants, flies and cockroaches. The baits include amino acids and a sugar. The baits can be combined with an insect toxicant to effectively control and eliminate insect populations. Methods for controlling insects using an insect bait of the invention are also disclosed.

9 Claims, 4 Drawing Sheets

INSECT BAIT

CROSS-REFERENCE TO RELATED APPLICATIONS

The present application claims the priority of U.S. provisional patent application No. 60/401,456 filed on Aug. 6, 2002.

FIELD OF THE INVENTION

The invention relates generally to the field of entomology. More particularly, the invention relates to methods and compositions for attracting and exterminating pests.

BACKGROUND

Ants are a common insect pest in and around the home as well as in agricultural settings. Various ant species pose significant problems in the home, including damage to wooden structures, roofs, and electrical equipment. Ant pests have also been known to introduce contamination and disease by spreading pathogens and some ant species inflict painful stings that can be life-threatening to sensitive individuals. In agriculture, some ants feed on germinating seeds and crop seedlings while some domesticate and protect other pest insects that feed on crops. Examples of pest ants include fire ants (*Solenopsis* spp.), argentine ants (*Linepithema humile*), pharaoh ants (*Monomorium pharaonis*), little black ants (*Monomorium spp.*), carpenter ants (*Camponotus* spp.), ghost ants (*Tapinoma* spp.), big-headed ants (*Pheidole* spp.) and white-footed ants (*Technomyrmex albipes*).

The white-footed ant was first collected from Indonesia, but has spread throughout the tropics and subtropical areas and is now found in Asia, Papua New Guinea, Guam, Australia, New Zealand, South Africa, Hawaii, and Florida. In recent years, reports of these ants infesting homes have increased considerably. These small ants exist in vast colonies, with colony size estimates ranging from 400,000 to over 1 million individuals. Due to their numbers and colonizing habits, these ants have become a nuisance to homeowners, and in some locations, these ants contribute to degradation of agricultural crops by protecting and nurturing insect pests, such as aphids and scales, that feed on the crops.

While white-footed ants are not directly harmful to humans, they are a nuisance within and around the home as well as a threat to crops. Several biological aspects of the white-footed ant make it a difficult pest to control, including the size of colonies, tremendous reproduction capabilities, and tiny body size allowing entry to most structures. Currently, no baits specific for the white-footed ant are commercially available. Since attempts to eradicate this pest have not been successful, the potential exists for the migration of these pests into previously uninhabited areas.

To control insect pests, formulations including both a bait (attractant) and an insect toxicant are generally employed. Most commercially available baits contain either a vegetable oil or a sugar as the attractant. Although various insect pest baits are currently available, the utility of these baits for the control of sugar-loving ants has been limited. Many species of ants have proven to be difficult to control with currently available baits, as the ants do not feed on the baits for sufficient periods of time, and the components of the baits degrade rather rapidly.

SUMMARY

An insect bait has been formulated that consists of sugar and amino acids at concentrations that have been found to be significantly preferred by ants. Examples of sugars that may be used in the present invention include sucrose, fructose, and glucose. Examples of amino acids that may be used in the invention include alanine, asparagine, aspartic acid, glutamic acid, glutamine, glycine, histidine, phenylalanine, proline, serine, threonine, and valine. The compositions and methods of the invention can be used in a number of applications.

For example, the compositions can be used to exterminate pest insects. For the extermination of pest insects, the insect bait is mixed with an insect toxicant. The compositions of the invention can be used to attract and control a wide array of different insects, including ants, flies, silverfish, and roaches. A preferred use of the invention is to control ants, particularly white-footed ants, ghost ants, argentine ants, fire ants and carpenter ants.

In other applications, including entomological research applications, the compositions of the invention can be used as insect feed. When placed in a container with insects, the compositions provide an attractive and nutritious food source. Accordingly, the invention features an insect bait that includes a plurality of amino acids, a sugar, and a preservative. The plurality of amino acids can have a concentration of about 2–7 g/100 ml of insect bait and include asparagine. The sugar can be sucrose, fructose, glucose, maltose, trehalose, honey, cane syrup or molasses and have a concentration of about 20–60 g/100 ml of insect bait. The preservative can be sodium benzoate, citric acid, disodium octaborate tetrahydrate (DOT), or a mixture of sodium benzoate and citric acid.

In another aspect, the invention features an insect bait including an insect toxicant.

The insect toxicant can be DOT, thiamethoxam, orthoboric acid, borax, imidacloprid, or indoxacarb. The insect toxicant can also be an insect growth regulator. The insect toxicant has a concentration of about 1–100 ppm of insect bait.

Within the invention is an insect bait including a plurality of amino acids, one of the amino acids being asparagine, and a sugar. The plurality of amino acids has a concentration of about 2–7 g/100 ml of insect bait. The sugar can be sucrose, fructose, glucose, maltose, trehalose, honey, cane syrup and molasses and have a concentration of about 20–60 g/100 ml of insect bait.

The insect bait can further include a preservative such as sodium benzoate, citric acid, DOT, or a mixture of sodium benzoate and citric acid. The insect bait can also include an insect toxicant such as DOT, thiamethoxam, orthoboric acid, borax, imidacloprid, indoxacarb, or an insect growth regulator. The insect toxicant can have a concentration of about 1–100 ppm of insect bait.

In still another aspect, the invention features several methods, including a method for controlling insects. This method includes the steps of: providing an insect bait including a plurality of amino acids, a sugar, and a preservative, and applying an effective amount of the insect bait to an area to be controlled. A variation of this method includes the steps of: providing an insect bait including a plurality of amino acids, a sugar, a preservative, and an insect toxicant, and applying an effective amount of the insect bait to an area to be controlled.

Also within the invention is a method for controlling insects at a location. This method includes the steps of: sampling from the location nectars and/or honeydews, determining compositions of the nectars and honeydews from the location, formulating a mimic from the compositions, combining the mimic with an insect toxicant, and applying an effective amount of the mimic and insect toxicant combination to the location.

Another method within the invention is a method for preparing a granular insect bait. This method includes the steps of: mixing a lipid-containing substance and an insect bait including a plurality of amino acids, a sugar and a preservative with a granular carrier until the carrier has absorbed at least a portion of the mixture, and subjecting the carrier to heat until the carrier retains about 8–13% moisture. In this method, the carrier can be corn grits and the lipid-containing substance can include an oil such as olive oil.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including any definitions will control. In addition, the particular embodiments discussed below are illustrative only and not intended to be limiting.

DETAILED DESCRIPTION

Figure 1:
FIG. 1 is a preference bioassay showing an arrangement of 6-ml feeding vials against a building exterior.
Figure 1:
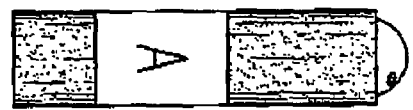
Figure 1:
Figure 1:
Figure 1:
Figure 1:
Figure 1:
Figure 1:
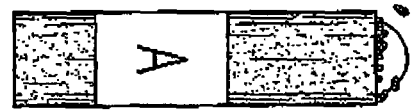
Figure 1:
Figure 1:

Studies have revealed the foraging and feeding mechanisms of many insect pest species. White-footed ants, like many other insect pests, are strongly attracted to sources of sugar. The insect bait of the present invention contains both sugar and amino acids at concentrations that have been found to be significantly preferred by ants in the field and in the laboratory, compared to several commercially available ant baits. As used herein, the terms "bait" and "attractant" mean any substance that will entice an insect to ingest that substance alone, or combined with one or more other substances, including an insect toxicant.

The insect bait of the present invention can include:
(a) a sugar such as, for example, sucrose, fructose, glucose, maltose, trehalose, honey, cane syrup, and molasses,
(b) a combination of amino acids, and
(c) a preservative.

The concentration of sugar in the insect bait is in the range of about 20–60 gram (g)/100 ml of bait with a preferable concentration of about 40 g/100 ml of bait. Sugars that may be used in the compositions of the invention include sucrose, fructose, glucose, maltose, trehalose, honey, and cane syrup. Sucrose can be used at a concentration in the range of about 25–50 g/100 ml of bait, fructose at a concentration in the range of about 5–40 g/100 ml of bait, glucose at a concentration in the range of about 5–20 g/100 ml of bait, maltose at a concentration in the range of about 5–20 g/100 ml of bait, and trehalose at a concentration in the range of about 1–20 g/100 ml of bait. A preferable amount of honey is in the range of about 1–25% of the total volume of the bait. A preferable amount of cane syrup is in the range of about 5–50% of the total volume of the bait, while a preferable amount of molasses is in the range of about 0.1–10% of the total volume of the bait.

The insect bait compositions can contain combinations of amino acids. Amino acids that may be used within the bait include, for example, alanine, asparagine, aspartic acid, glutamic acid, glutamine, glycine, histidine, phenylalanine, proline, serine, threonine, and valine. A preferred amino acid to be used in the insect bait is asparagine. The concentration of each amino acid as well as the concentration of total amino acids in the bait is in an amount which enhances the gustatory stimulation of insects by the bait. Each amino acid may be present in concentrations of about 0.025–5.0 g/100 ml of bait, with a preferred range of about 0.04–3.0 g/100 ml of bait. For example, asparagine may be present in concentrations of 1.0–5.0 g/100 ml with a preferred range of about 2.0–3.0 g/100 ml. The amino acids may be present in combined concentrations of 2–7 g/100 ml of bait with a preferred range of about 3–4 g/100 ml. A preferred bait formulation contains alanine at a concentration of about 0.05 g/100 ml; asparagine at a concentration of about 2.50 g/100 ml; aspartic acid at a concentration of about 0.20 g/100 ml; glutamic acid at a concentration of about 0.10 g/100 ml; glutamine at a concentration of about 0.10 g/100 ml; glycine at a concentration of about 0.05 g/100 ml; histidine at a concentration of about 0.05 g/100 ml; phenylalanine at a concentration of about 0.05 g/100 ml; proline at a concentration of about 0.05 g/100 ml; serine at a concentration of about 0.10 g/100 ml; threonine at a concentration of about 0.10 g/100 ml; and valine at a concentration of about 0.10 g/100 ml. In addition to or in place of amino acids, other nitrogenous compounds such as uric acid and urea may be included in the ant bait. Insects show a preference for food sources containing nitrogen, such as found in uric acid, urea, and amino acids. Nitrogenous compounds such as uric acid and urea may be added to the ant bait of the invention at a concentration in the range of about 0.5 g/100 ml of bait to 5.0 g/100 ml of bait.

Preservatives that are effective in maintaining the integrity of the bait from microbial action may be used with the bait and are contemplated to be within the scope of this invention. The concentration of preservative in the ant bait can be about 0.015–7.5 g/100 ml of the insect bait with a preferred range of about 0.02–5.5 g/100 ml of bait. A preferred preservative, for example, is sodium benzoate mixed with citric acid. If the preservative is a combination of sodium benzoate and citric acid, a preferable amount of sodium benzoate is in the range of about 0.02–0.06 g/100 ml of the insect bait and a preferable amount of citric acid is in the range of about 0.20–0.5 g/100 ml of the insect bait. DOT (Tim-bor, U.S. Borax, Inc., Los Angeles, Calif.) may also act as a preservative when combined with the insect bait. DOT may be used as an effective preservative at a concentration in the range of about 1–6 g/100 ml of the bait.

In addition to amino acids, sugars and preservatives, insect bait compositions of the invention can include lipid-containing substances, such as fats and oils. Any type of fat or oil may be added to an insect bait composition. Fats that may be used include coco butter, vegetable fats, and kernel fats, for example. A non-exhaustive list of oils includes soybean oil, safflower oil, corn oil, coconut oil, sunflower oil, peanut oil, and vegetable oil. Oils and fats may be used at concentrations ranging from about 0.5–10.0 g/100 ml of bait. Incorporation of a lipid-containing substance into an insect bait composition is particularly useful for attracting some insects such as fire ants, for example.

In a preferred application, the insect bait of the invention is used with insect toxicants for extermination of pest insects. A preferred toxicant to be used in combination with the insect bait of the invention is Thiamethoxam (Syngenta Crop Protection, Greensboro, N.C.). Thiamethoxam can be used as a toxicant at concentrations of 1–100 ppm (parts per million) in insect bait, with a preferred range of about 5–25 ppm in insect bait. A preferred bait formulation for exterminating insects contains Thiamethoxam at a concentration of about 10 ppm in insect bait. Another example of a suitable insect toxicant includes DOT, which may be present in concentrations of about 1–6 g/100 ml of bait for the extermination of insect pests. A preferred concentration of DOT for the extermination of pest insects is about 2 g/100 ml of bait. DOT may be used as both an effective insect toxicant and an effective preservative of the bait. If DOT is used as both an insect toxicant and a preservative, a preferable amount of DOT is used in concentrations of about 3–7 g/100 ml of bait, with a preferable concentration of about 5 g/100 ml of bait. Suitable insect toxicants can also include insect growth regulators, orthoboric acid, borax, Imidacloprid (Bayer Environmental Science, Montvale, N.J.) and indoxacarb (Dupont, Wilmington, Del.). Insect toxicant concentrations range from about 0.01–12 g/100 ml of the insect bait.

The mixture of insect bait and insect toxicant is placed in areas in which the insects are to be controlled, such as around crop plants, commercial establishmnents, and residences. In some applications, the mixture of insect bait and insect toxicant can be applied to an area once for the control of insect pests. In other applications, the mixture of insect bait and insect toxicant are applied to an area more than once, for example, every few days. The amount of mixture to be used for a given area depends on the size of the insect population and the type of insect to be controlled. Suitable amounts of the mixture for controlling insect pests can be readily determined by one of ordinary skill in the art. A suitable amount of insect bait is an amount that provides sufficient bait such that at least a majority of insects (e.g., 51, 55, 60, 65, 70, 75, 80, 85, 90, 95, 100%) in a group or nest consumes the bait. For example, the rate of consumption of the insect bait by a particular group or nest of insects can be measured by placing a container of insect bait of the invention close to or on a trail of the insects and taking regular measurements of insect bait consumed.

In another embodiment, the insect bait is useful as an insect feed. The insect bait can be used as an insect feed in entomological laboratories, for example. When placed in a container with nesting insects, the insect bait is a nutrient for the insects. As an insect feed, a suitable amount of insect bait can be determined by one of ordinary skill in the art based on the size and numbers of the insects to be fed.

In yet another embodiment, natural flavors are added to the insect bait to enhance the odor and/or taste of the insect bait. For example, extracts of fruits and flowers can be added to the insect bait. Examples of preferred fruits and flowers include coconut, gardenia, hibiscus, citrus, and mango.

In preferred embodiments, insect bait compositions of the invention are prepared using any of a number of methods for eliminating microorganisms from the compositions. In the absence of microorganisms, the integrity of a composition is preserved for a greater period of time compared to a composition containing microorganisms. One method of eliminating microorganisms is to pasteurize the composition, i.e., expose the composition to an elevated temperature for a period of time sufficient to destroy microorganisms without substantially altering taste or quality of the composition. For example, to pasteurize an ant bait composition, the composition is heated to a temperature in the range of about 60° C. to 70° C. (e.g., 63° C.) for 30 minutes. Another method of eliminating microorganisms involves passing the composition through a filter. A variety of filters and filtration systems for removing microorganisms from a sample are commercially available, e.g., those from Nalgene (Rochester, N.Y.) and Millipore (Bedford, Mass.). Alternatively, microorganisms may be killed by autoclaving the composition. A combination of filtering and autoclaving may also be useful for killing microorganisms within the composition. For example, prior to mixing a solution containing amino acids with a solution containing sugars to prepare an ant bait composition, the solution containing amino acids is passed through a filter, while the solution containing sugars is autoclaved.

The insect bait compositions of the invention can take any form, such as liquids, gels, granules, and emulsions. The choice of formulation is dependent upon a number of criteria, including size, feeding preference, and nesting habit of the insect to be attracted and exterminated. Some ants, including white-footed ants, consume liquid baits more efficiently than they consume other forms of bait such as gels and emulsions. Therefore, to attract and exterminate ants (e.g., white-footed ants), the insect bait can be formulated as a liquid. The insect bait can be formulated as granules, however, to attract other types of ants such as fire ants. Because fire ants are present in multiple nests spanning a large area, a granular insect bait is best suited for distributing insect bait to a population of fire ants due to the ease with which granules can be distributed over a large area. Granular formulations may be particularly useful for killing a nest of insects, as granules are typically small particles that can be picked up and transported by insects back to their nests.

For attracting and exterminating cockroaches, a gel or emulsion formulation is preferred, as gels and emulsions are administered to cockroaches more conveniently than liquids. For example, gels and emulsions are conveniently packaged in tubes and injected into cracks and crevices where cockroaches typically nest. Similarly, insect bait formulated as an emulsion or gel is preferred for attracting and exterminating flies.

Any number of methods can be used to prepare insect bait compositions of the invention. The method employed is dependent upon the type of formulation to be prepared, e.g., liquid vs. emulsion vs. granules, etc. A preferred composition of insect bait is a liquid formulation and is recited below in Table I. To prepare insect bait as a liquid formulation, each component listed in Table I is weighed and added to a flask containing water as a solvent. The contents of the flask are heated and stirred until sufficiently dissolved.

A granular formation of insect bait useful for attracting ants such as fire ants, big-headed ants and carpenter ants may be prepared using any suitable method. Typically, a granular formulation is prepared by mixing an oil (e.g., olive oil) or a fat with a liquid formulation of the insect bait of the invention. In a preferred embodiment, olive oil (e.g., Pompeian brand olive oil, Baltimore, Md.) is used, as experiments have shown that olive oil is consumed more by fire ants than other oils tested. Once the oil and insect bait solution are emulsified (e.g., by heating and stirring), a thickening agent (e.g., lecithin) is added. A thickening agent is any agent that increases the viscosity of the composition. Emulsifiers, for example, may be used as thickening agents. Examples of emulsifiers and thickening agents include polysorbate 20, xanthan gum, glycerol, gum arabic, Irish moss, cellulose gum, locust bean gum, agar, and lecithin. Such emulsifiers and thickening agents may be flavored with coconut or hibiscus flowers to further enhance attraction properties of the insect bait composition. The resultant emulsion is then contacted with (e.g., sprayed onto) a suitable carrier.

A suitable carrier is any carrier that can be ingested by an insect and that has the ability to absorb at least a portion of the emulsion to which the carrier is contacted. Defatted corn grits are a preferred carrier because they are readily available and have been used successfully in the control of fire ants. Defatted corn grits have also been shown to maintain their integrity better after exposure to rain than other carriers. Nonetheless, other carriers such as non-defatted corn grits, peas, and beans such as garbanzo beans may also be used. The carrier is contacted with the emulsion for a time period sufficient for the carrier to absorb the emulsion. The carrier is then dried to evaporate off excess moisture, resulting in granules that have retained some moisture. The level of moisture retained in the carrier is important for optimal insect attracting. If the carrier retains too much moisture, the bait and/or carrier will decay. Conversely, if the carrier retains insufficient moisture, insects are not attracted to the bait. An optimal range of moisture to be retained in the carrier is about 8–13% moisture.

An example of a protocol for preparing a granular formation is as follows. First, about 10 ml of oil (e.g., olive oil) are added to a container (e.g., a flask). Approximately 5 ml of insect bait (e.g., the insect bait of Table I minus sucrose) are then added to the container, and the contents of the container are stirred and heated (e.g., by placing the container on a stirring hot plate heated to less than 100° C.). While the contents are being stirred, up to 10 drops (e.g., 5 drops) of a thickening agent (e.g., lecithin) are added until the contents are emulsified. The resultant emulsion is then contacted with (e.g., sprayed onto) approximately 25 g of defatted corn grits. The grits are stirred and allowed to sit until they have absorbed the liquid (e.g., 30 minutes). The grits are then dried in an oven at low heat to evaporate off excess moisture, resulting in granules that have retained about 8–13% moisture.

An alternative protocol for preparing a granular formulation involves contacting the insect bait composition and oil to the carrier separately, rather than combining the insect bait composition and oil prior to contacting them with the carrier. A variation of this granular formulation can be prepared for attracting and killing ants. In this variation, a toxicant (e.g., Thiamethoxam, Imidacloprid) at a concentration of about 100–250 ppm is added to the container prior to stirring and heating.

To prepare an emulsion formulation, the protocol for preparing a granular formulation may be used with some modifications. A first modification involves adding a second thickening agent such as gum arabic or corn starch to the mixture of oil, insect bait and first thickening agent (e.g., lecithin). A second modification is the removal of the step of contacting the emulsion to a carrier.

The foregoing formulations can be made by any method. The concentrations, temperatures, and time periods described above can be determined using standard laboratory procedures. Pasteurization and emulsification methods, for example, are commonly known in the art. Sugar, toxicant, amino acid, emulsifier, thickening agent, carrier and oil concentrations may vary depending upon the formulation employed and the type of insect to be attracted and/or killed.

The insect bait compositions of the invention can be formulated to mimic the nectars and honeydews on which ants and other insects feed, that is, to substantially duplicate the amino acid and sugar compositions of such honeydews and nectars. The compositions of nectars and honeydews can vary from location to location. In one aspect of the invention, the insect bait compositions of the invention can be used to attract and exterminate insects on a localized basis, for example, in particular geographic locations. To attract and exterminate insects on a localized basis, the nectars and honeydews from a particular location are sampled and their compositions are determined. An insect bait that mimics the nectar and honeydew compositions of that location is formulated by combining a sugar and a combination of amino acids at concentrations that are substantially similar or identical to those found in the nectars and honeydews of that location. Alternatively, the compositions of the invention can be formulated so as to produce substantially similar feeding patterns as compared to the nectars or honeydews from a given location. Such formulations could be determined empirically by conducting comparative feeding tests between the formulations and the native nectars and honeydews. The insect bait is then combined with an insect toxicant. When administered to the particular area, the insect bait and toxicant mixture attracts and exterminates insects localized to that particular area.

TABLE I

| AMINO ACIDS/SUGAR | g/100 ml |
|---|---|
| Alanine | 0.05 |
| Asparagine | 2.50 |
| Aspartic Acid | 0.20 |

TABLE I-continued

| AMINO ACIDS/SUGAR | g/100 ml |
|---|---|
| Glutamic Acid | 0.10 |
| Glutamine | 0.10 |
| Glycine | 0.05 |
| Histidine | 0.05 |
| Phenylalanine | 0.05 |
| Proline | 0.05 |
| Serine | 0.10 |
| Threonine | 0.10 |
| Valine | 0.10 |
| Sucrose | 40.00 |

EXAMPLES

The present invention is further illustrated by the following specific examples. The examples are provided for illustration only and are not to be construed as limiting the scope or content of the invention in any way.

Example 1

Preference Test Study

Two-choice, random-order preference tests were performed on the exterior walls at the University of Florida Fort Lauderdale Research and Education Center, Broward County, Fla. Two commercial ready-to-use (RTU) ant baits and several sugar solutions were tested with and without active ingredients, including 10,000 ppm DOT (Uncle Albert's Super Smart Ant Bait®, A Safe Pest Eliminators, Inc., Miami, Fla.) and 10,000 ppm orthoboric acid (Drax Liquidator®, Waterbury Companies, Inc., Waterbury, Conn.). Sugar water solutions tested included: 100,000 ppm, 150,000 ppm, 200,000 ppm, 250,000 ppm, 350,000 ppm, 400,000 ppm, and 500,000 ppm sucrose (Publix Supermarkets, Lakeland, Fla.), 250,000 ppm and 500,000 ppm fructose (Fisher Scientific, Pittsburgh, Pa.), 250,000 ppm maltose (Fisher Scientific). Four insect bait formulations of the invention (ND 1, ND2, ND3, ND4, see Table II) were also tested against sugars and commercial baits. Solutions of sucrose and DOT were made from 98% DOT (Tim-borg®, U.S. Borax, Los Angeles, Calif.).

TABLE II

| AMINO ACIDS, SUGARS, PRESERVATIVES | g/100 ml ND1 | g/100 ml ND2 | g/100 ml ND3 | g/100 ml ND4 |
|---|---|---|---|---|
| ALANINE | 0.05 | 0.05 | 0.05 | 0.05 |
| ASPARAGINE | 2.36 | 2.50 | 2.50 | 2.50 |
| ASPARTIC ACID | 0.16 | 0.20 | 0.00 | 0.20 |
| CYSTEINE | 0.02 | 0.05 | 0.05 | 0.00 |
| GLUTAMIC ACID | 0.07 | 0.10 | 0.00 | 0.10 |
| GLUTAMINE | 0.09 | 0.10 | 0.10 | 0.10 |
| GLYCINE | 0.01 | 0.05 | 0.05 | 0.05 |
| HISTIDINE | 0.03 | 0.05 | 0.05 | 0.05 |
| PHENYLALANINE | 0.05 | 0.05 | 0.05 | 0.05 |
| PROLINE | 0.05 | 0.05 | 0.05 | 0.05 |
| SERINE | 0.11 | 0.10 | 0.10 | 0.10 |
| THREONINE | 0.08 | 0.10 | 0.10 | 0.10 |
| VALINE | 0.07 | 0.10 | 0.10 | 0.10 |
| SUCROSE | 20.00 | 10.00 | 35.00 | 40.00 |
| GLUCOSE | 0.00 | 10.00 | 0.00 | 0.00 |
| FRUCTOSE | 0.00 | 5.00 | 0.00 | 0.00 |
| preservatives mix 2-2 | | | | |
| Sodium benzoate | 0.025 | 0.025 | 0.025 | 0.025 |
| citric acid | 0.225 | 0.225 | 0.225 | 0.225 |

Glass shell vials (6-ml capacity) with Titesealt® plastic caps (Fisher Scientific) were used for bait containers. Vials were modified for use as bait containers by drilling holes (6 mm) in the caps, inserting cotton dental wicks, which minimize bait desiccation and entrapment by ants, adding 4.5-ml solution, and using Handi-tak® (Pacer Technology, Rancho Cucamonga, Calif.) adhesive putty to hold the vials on the walls. Each test consisted of 5 bait vial pairs placed in 2 columns (FIG. 1). Column positions (left and right) were chosen randomly so that ants had an unbiased likelihood of encountering either of the products being tested. Nine counts of ants on each wick were taken approximately every 30 minutes over 4.5 hours. When the numbers of ants could not be counted visually, digital photographs were taken, and counts were taken from a computer display. Data were analyzed using t-Test and Mann-Whitney Rank Sum Tests at P=0.05.

Figure 2:
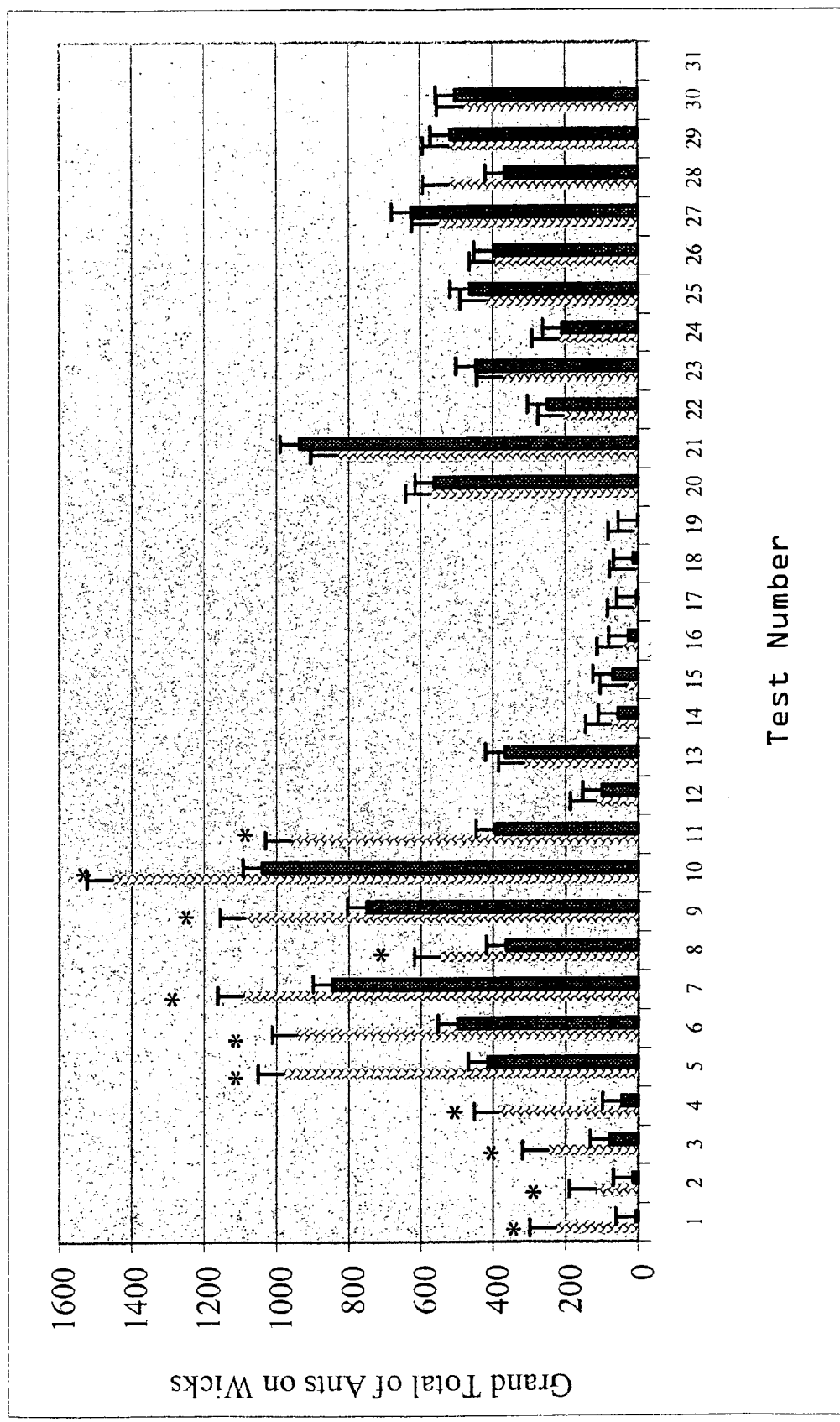
FIG. 2 is a graph of white-footed ant binary choice preference tests. Tests (total+SE) (n=5 replicates per pair). Insect bait formulations of the invention are denoted ND 1, ND2, ND3, and ND4. Test 1:10% Sucrose vs. water; Test 2:25% Fructose vs. 25% Maltose; Test 3:25% Sucrose vs. 10% Sucrose; Test 4:25% Sucrose vs. 25% Fructose; Test 5:25% Sucrose vs. 15% Sucrose; Test 6:25% Sucrose vs. 20% Sucrose; Test 7:40% Sucrose vs. ND1; Test 8:ND1 vs. 25% Sucrose; Test 9:ND3 vs. 35% Sucrose; Test 10:ND4 vs. 40% Sucrose; Test 11:ND4+1% DOT vs. Uncle Albert's Super Smart Ant Bait (A Safe Pest Eliminators, Inc., Miami, Fla.); Test 12:25% Sucrose vs. 25% Sucrose+2% ETOH; Test 13:25% Sucrose vs. Uncle Albert's Super Smart Ant Bait (A Safe Pest Eliminators, Inc., Miami, Fla.) (no active ingredient); Test 14:25% Fructose vs. Drax Liquidator (Waterbury Companies, Inc., Waterbury, Conn.) (no active ingredient); Test 15:25% Sucrose vs. 50% Sucrose; Test 16:25% Fructose vs. Uncle Albert's Super Smart Ant Bait (A Safe Pest Eliminators, Inc., Miami, Fla.) (no active ingredient); Test 17:50% Fructose vs. 50% Glucose; Test 18:25% Sucrose vs. 25% Maltose; Test 19:25% Sucrose vs. 25% Glucose; Test 20:ND1 vs. ND2; Test 21:ND2 vs. ND3; Test 22:Drax Liquidator (Waterbury Companies, Inc., Waterbury, Conn.) vs. 25% Sucrose+5% DOT; Test 23:Drax Liquidator (Waterbury Companies, Inc., Waterbury, Conn.) vs. 40% Sucrose+5% DOT; Test 24:25% Sucrose vs. 25% Sucrose+ 1% DOT; Test 25:25% Sucrose vs. 25% Sucrose+2% DOT; Test 26:25% Sucrose vs. 25% Sucrose+3% DOT; Test 27:25% Sucrose vs. 25% Sucrose+4% DOT; Test 28:25% Sucrose vs. 25% Sucrose+5% DOT; Test 29:25% Sucrose vs. 25% Sucrose+6% DOT; Test 30:25% Sucrose vs. 25% Sucrose+7% DOT.

FIG. 2 shows preference comparisons between solutions of sucrose, fructose, maltose and commercial bait carriers. Pairs 1–11 marked with asterisk totals differed significantly at P<0.05. t-Test and Mann-Whitney Rank Sum Test. Insect bait formulations of the invention used in the comparison are denoted ND1, ND2, ND3, and ND4.10% sucrose was highly preferred (P<0.001) over de-ionized water (test 1). Fructose was preferred over maltose at 25% each (P=0.033, test 2) while 25% sucrose was preferred over 25% fructose. (P<0.001, test 4). 25% sucrose was preferred over 10, 15 and 20% sucrose (tests 3, 5, and 6, respectively). Comparing ND1 with sucrose solutions, 40% sucrose was preferred over ND1 (P=0.002, test 7), but ND1 was preferred over 25% sucrose (P=<0.001, test 8). ND3 was preferred over 35% sucrose (P=0.020, test 9) and ND4 was preferred over 40% sucrose (P=0.015, test 10). ND4 containing 1% DOT was highly preferred over the commercial product, Uncle Albert's Super Smart Ant Bait® (DOT) having 1% DOT (P=<0.001,test 11).

White-footed ants showed no preference (P=0.968) between 2% ETOH+25% sucrose over 25% sucrose (test 12). There were no significant preferences between 25% sucrose or 25% fructose vs. Uncle Albert's Super Smart Ant Bait® (P=0.458, test 13 and P 0.057, test 16, respectively), 25% fructose vs. Drax® (P=0.580, test 14), or 25% sucrose solutions vs. 1% DOT+25% sucrose (P=0.569, test 24). Interestingly, there was no significant preference between 25% and 50% sucrose (P=0.112, test 15). There were no significant preferences between Drax® and 25 or 40% sucrose (P=0.394, test 22 and P=0.245, test 23, respectively). There were no significant preferences between ND1 and ND2 (P=0.844, test 20) as well as between ND2 and ND3 (P=0.713, test 21). There were no significant preferences for 25% sucrose vs. 25% glucose (P=0.463, test 19), 25% sucrose vs. 25% maltose (P=0.852, test 18) and 50% fructose vs. 50% glucose (P=0.817, test 17). There were no observed preferences with increasing concentrations of DOT, from 1% to 7% in 1% increments, vs. 25% sucrose (P=0.218 to 0.916, tests 24–30, respectively). Concentrations higher than 7% DOT were not tested.

Example 2

Laboratory Efficacy Tests

White-footed ants were collected from a stand of *Phoenix roebelenii* palms at the University of Florida Fort Lauderdale Research and Education Center (Broward Co., FL). Adult ants and brood were collected from nesting sites in palm thatch between 9 a.m. and 3 p.m., when most of the foragers are in the nests. The thatch was placed in a plastic 100-liter garbage pail through a 28-cm hole cut into the center of its lid. The upper portions of the interior sides of the pail were coated with a petroleum jelly (Vaseline® London, UK) to retard the ants' escape.

Figure 3:
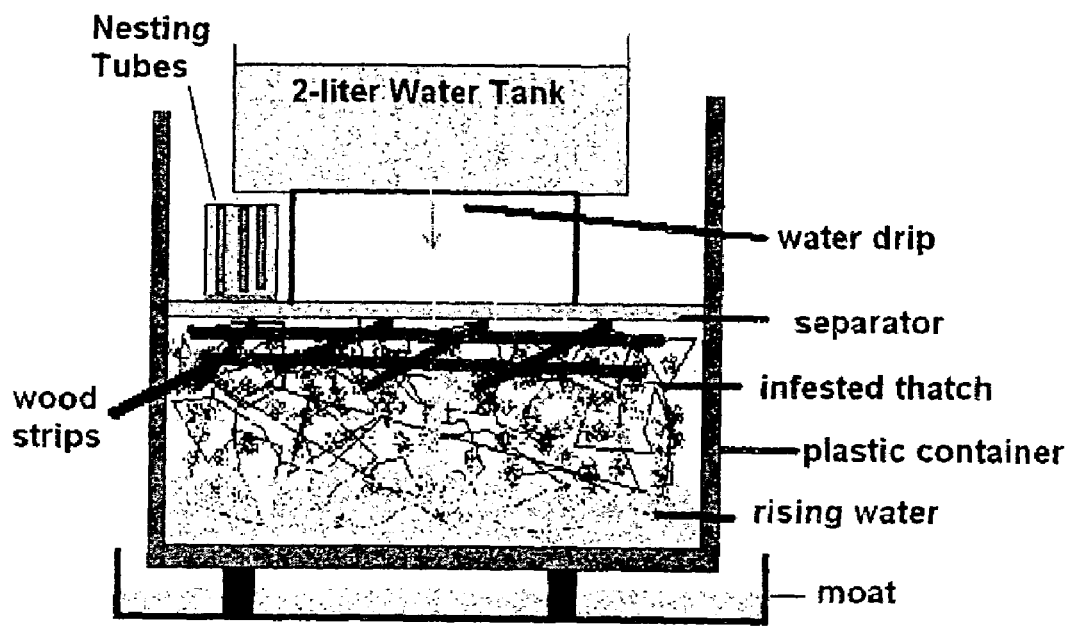
FIG. 3 shows a device used to displace ants from palm thatch to nesting tubes.

Ants were separated from thatch material in the laboratory using a plastic container (30×23×10 cm) which was supported over a water moat (FIG. 3). Infested thatch material was taken from the garbage pail, placed in the container, covered with 1×15-cm strips of wood and a separator sheet of 3-mm polycarbonate with 2-mm holes. Dripping water from a 2-1 tank suspended over the container forced the ants to leave the thatch and enter nesting tubes (10×75 mm clear polystyrene test tubes) (Fisher Scientific, Pittsburgh, Pa.), filled at the bottom with a small cotton ball soaked with sugar water, and completely covered with aluminum foil. Six nesting test tubes were sandwiched between Styrofoam panels and when the tubes were filled with workers and brood, they were placed in a 37-1 holding tank provisioned with 25% (w/v) aqueous sucrose and chicken baby food (Chicken & Chicken Broth, Beech-Nut Nutrition Corp., Canajoharie, N.Y.).

Figure 4:
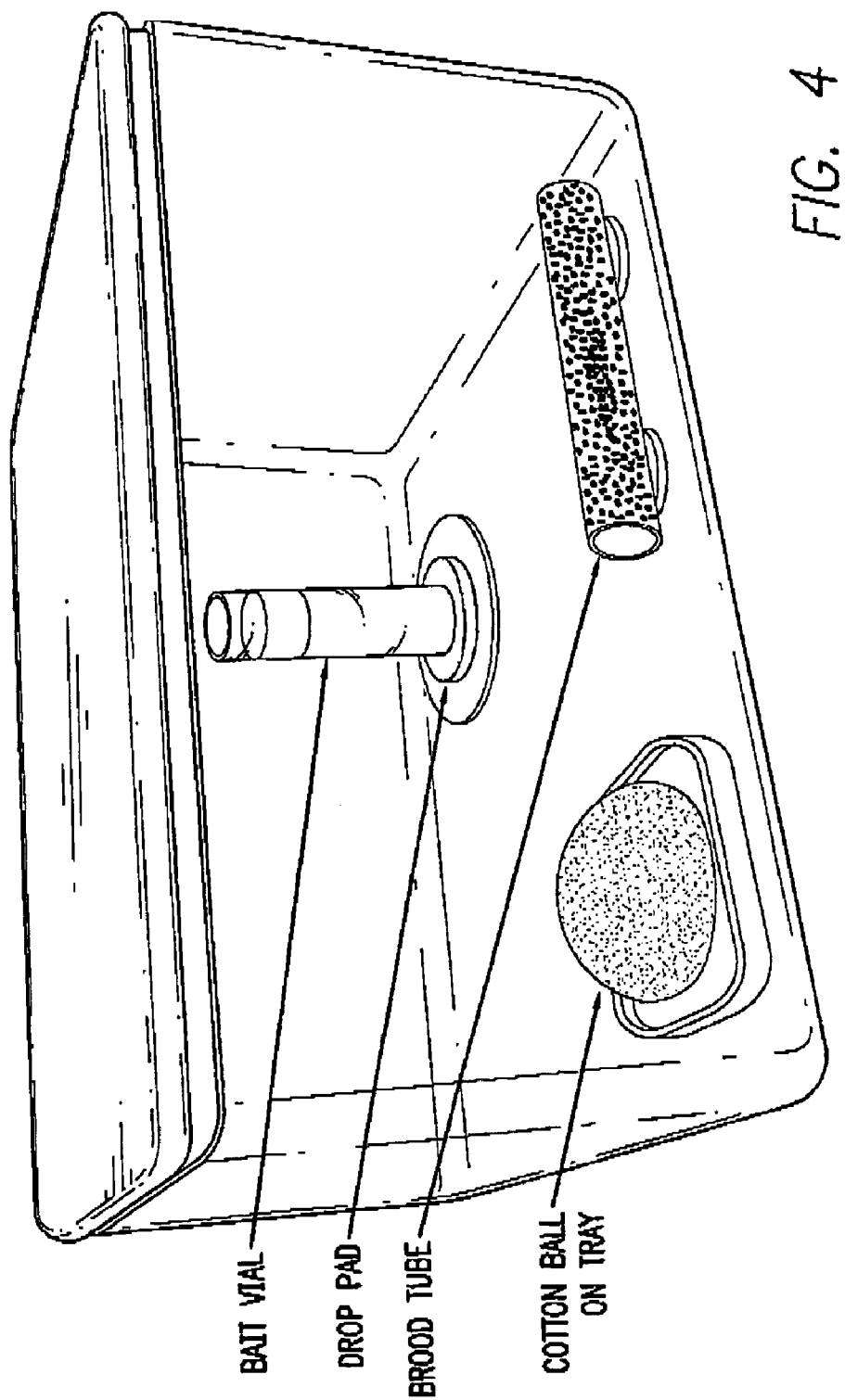
FIG. 4 shows a laboratory colony box used for a WFA efficacy test.

Nalgene™ reusable plastic utility boxes with lids (19× 16×10 mm) (Fisher Scientific, Pittsburgh, Pa.) were used to hold white-footed ant colonies for laboratory tests (FIG. 4). Nesting tubes with about 200 ants and dozens of brood were placed into each box, held in place with a small amount of Handi-Tak®. Ants were provisioned with water by placing a small cotton ball moistened with approximately 2-ml deionized water in a 41×41×8 mm plastic weighing boat.

Sugar water (25% sucrose w/v) and toxic liquid baits (see below) were fed via 6-ml glass shell vials with Titeseal® plastic caps. Five holes (0.86 mm ID) were drilled into the caps. Vials were filled with 4.5 ml bait solution, inverted, and attached to the sides of the boxes with Handi-Tak® (FIG. 3). Sugar water was fed ad libitum to the ants at all times and supplemented twice weekly by live termites or canned chicken for protein. A felt pad was placed under each vial to catch errant drops and prevent ants from being entrapped in their sticky residue. Ants were allowed to acclimatize in boxes for several weeks. Each day dead ants were removed and replaced with live ants. When ant populations appeared stable, treatments were applied. No ants were added during the experiment.

Fourteen treatments (5 replicates each, assigned randomly) were applied to the ants in boxes. Liquid baits included 1 and 10 ppm Thiamethoxam in 25% aqueous sucrose solution, 50 ppm Imidacloprid in 25% aqueous sucrose solution, 10,000 ppm orthoboric acid (Drax Liquidator®) RTU bait, 54,000 ppm sodium borate decahydrate (Terro Ant Killer II®, Senoret Chemical Co. Minneapolis, Minn.) RTU bait, 10,000 ppm DOT (Tim-bor®) in ND4. Surface treatments included 600 ppm fipronil (Termidor® SC, Aventis Environmental Science, Montvale, N.J.), 800 ppm spinosad, (Conserve® SC, Dow AgroSciences, Indianapolis, Ind.), and 600 ppm bifenthrin (Talstar®, FMC Corporation, Philadelphia, Pa.). Additional treatments included 5,000 ppm XR-007 SC (Dow AgroSciences), made into a loose gel using 5,000 ppm gellan gum (Phytagel®, Sigma, St. Louis, Mo.) in 25% sucrose-water (wt/wt), Ultrasonic Pest Repellers (Lentek International, Inc., Orlando, Fla.) untreated controls included 25% sucrose solution, surface and gellan gum (Phytagel®) applications. The suspension of XR-007 was placed into a plastic weighing boat (0.5 g), and replaced twice a week or when it desiccated. One corner was cut away to allow for easier access by the ants.

In a second trial 15 treatments (5 replicates each, assigned randomly) were applied to the ants in boxes. Liquid baits included 10 ppm Thiamethoxam in ND4 solution, 50 ppm Imidacloprid (Pre-Emptg) RTU bait, 50 ppm Imidacloprid ant bait instant granules (Bayer Environmental Sciences, Montvale, N.J.) in deionized water (3: 1, water: granules), and 54,000 ppm DOT (Whitmire Micro-Gen Research Laboratories, Inc., St. Louis, Mo.) RTU ant bait. Surface treatments included 1,200 ppm fipronil (Termidor®& SC), 500 ppm indoxacarb (DuPont, Wilmington, Del.), 500 ppm deltamethrin (DeltaDust®, Aventis Environmental Science), and 600 ppm lambda cyhalothrin (Demand®V CS, Syngenta Crop Protection). Additional treatments included 10 ppm fipronil (Maxforce® Ant Bait Gel, Maxforce Insect Control Systems, Oakland, Calif.), 100 ppm fipronil (Combat® Quick Kill over-the-counter ant bait stations, Combat Insect Control Systems, Oakland, Calif.), 5,000 ppm XR-007 SC (Dow AgroSciences), used as a suspension bait in honey-water (1:1), 500 ppm indoxacarb (DuPont, Wilmington, Del.) as a suspension in honey-water (1:1), and liquid bait, surface, and gel untreated controls.

Each box to receive a liquid bait treatment also contained a 25% aqueous sucrose vial on the right rear wall, along with the toxic bait vial on the left side of the rear colony box wall. Both vials had felt pads under them. Boxes with gels had the gels in weighing boats. The boats were on the left side of the box, and the untreated sugar water vials were on the right side. Surface treatments were applied to run-off at label or manufacturer-suggested concentration to basswood panels (5×7.7 cm) that were previously painted with white acrylic paint to simulate a typical house exterior. This was accomplished by adding 0.17-ml to panels and distributing the solution evenly with a fine paintbrush previously saturated in solution. One-half g XR-007 and indoxacarb in honey were placed into the bulb of 9.3-ml large-tip opening transfer pipettes (having had 8-cm cut back from the tip, Samco®, San Fernando, Calif.). The treatment preparation of Imidacloprid ant bait instant granules was done in non-randomized colony boxes because the product was received 1 day after the test had begun.

Dead ants were removed and counted daily for the first week, then twice weekly thereafter. At the end of the experiment, all ants still living were killed with ethanol and counted to determine the total number of ants in each box. It was assumed that the numbers of adults that emerged from pupae in the boxes were not significant over the seven-week trial. Mean percent mortalities were analyzed by ANOVA (analysis of variance) and general linear model (SAS Institute, 1989 SAS/STAT user's guide, version 6, 4th ed. SAS Institute, Cary, N.C.) and means separated using Student-Newman-Keals test at $P<0.05$.

Mortality for the first trial was recorded for 51 days. Mean percent mortality for each treatment at 1, 3, 7, 30 and 51 days after exposure were selected to be representative of the exposure time course and are given in Table III.

One day after exposure, bifenthrin (Talstarg®, FMC Corporation, Philadelphia, Pa.) had the highest mean mortality (8%), but it was not significantly greater than Imidacloprid (Exempt®) (5%), Thiamethoxam 10 ppm (4%), ND4 (4%) or XR-007 (4%), and only Talsar®'s percent mortality was significantly greater than the controls. Three days after exposure, percent mortality was significantly greater for ND4 at 27%, and ND4 was significantly greater than all other treatments. On day 7, the percent mortality for ND4 continued to be significantly greater at 49% than all other treatments. The second highest group on day 7 consists of Thiamethoxam 10 ppm (39%) and Imidacloprid (30%), which is not significantly greater than sodium borate decahydrate (Terro Ant Killer II®, Senoret Chemical Co. Minneapolis, Minn.) (21%).

After 30 and 51 days, Imidacloprid (79% and 91%), ND4 (77% and 87%), Thiamethoxam 10 ppm (65% and 84%) and sodium borate decahydrate (Terro Ant Killer®) (64% and 76%) were the only treatments that were significantly different than the controls.

TABLE III

Mean percent Mortality (+/SD) of *T. Albipes* adults after 1, 3, 7, 30 and 51 days exposure to 14 treatments in a non-forced bioassay.

| | Days | | | | |
|---|---|---|---|---|---|
| | 1 | 3 | 7 | 30 | 51 |
| Treatment | | | | | |
| Talstar | 7.60 ± 3.10a | 11.69 ± 5.47bcd | 14.13 ± 3.92de | 28.48 ± 4.44bc | 46.77 ± 7.35bc |
| Imidacloprid | 4.92 ± 4.02ab | 14.06 ± 7.40b | 29.84 ± 10.63bc | 78.55 ± 4.83a | 90.86 ± 5.43a |
| Thiamethoxam 10 ppm | 4.44 ± 2.26ab | 18.33 ± 8.49b | 38.81 ± 11.13b | 64.77 ± 15.51a | 84.40 ± 10.09a |
| ND4 | 4.07 ± 3.10ab | 26.55 ± 13.36a | 48.81 ± 14.86a | 76.99 ± 11.43a | 86.95 ± 6.05a |
| XR007 | 3.63 ± 2.17ab | 5.44 ± 2.48cd | 10.22 ± 4.97de | 27.25 ± 8.69bc | 42.96 ± 11.78bcd |
| Terro | 3.17 ± 4.66b | 6.83 ± 5.80cd | 21.22 ± 9.22cd | 63.94 ± 7.99a | 75.51 ± 7.01a |
| Thiamethoxam 1 ppm | 1.66 ± 1.17b | 3.64 ± 2.80cd | 6.44 ± 4.73e | 19.73 ± 9.98c | 44.02 ± 13.73bcd |
| Control bait | 1.37 ± 0.73b | 2.81 ± 0.98cd | 4.72 ± 1.34e | 18.33 ± 4.19c | 38.82 ± 5.25bcd |
| Control surface | 1.36 ± 0.63b | 3.73 ± 1.72cd | 5.71 ± 2.05e | 24.24 ± 6.65bc | 43.99 ± 7.07bcd |
| Drax | 1.23 ± 1.16b | 4.79 ± 4.14cd | 15.37 ± 13.16de | 37.68 ± 12.88b | 54.18 ± 12.16b |
| Pest repeller | 1.05 ± 0.67b | 4.49 ± 4.08cd | 6.46 ± 4.24e | 14.23 ± 9.05c | 27.79 ± 13.20d |
| Spinosad | 1.01 ± 0.87b | 2.02 ± 0.83d | 3.78 ± 1.85e | 16.15 ± 3.78c | 34.51 ± 2.42cd |
| Fipronil | 0.98 ± 0.70b | 3.46 ± 1.38cd | 6.76 ± 2.25e | 27.88 ± 5.89bc | 53.76 ± 10.84b |
| Control gel | 0.88 ± 0.39b | 2.11 ± 0.88d | 5.26 ± 2.07e | 19.29 ± 7.91c | 38.97 ± 12.08bcd |
| Treatment Effects Statistics | | | | | |
| F | 3.99 | 8.72 | 17.28 | 35.84 | 24.33 |
| df | 13, 70 | 13, 70 | 13, 70 | 13, 70 | 13, 70 |
| P | 0.0001 | 0.0001 | 0.0001 | 0.0001 | 0.0001 |

[a]Means of 5 replicates, mean = 202.49, SD = 68.41. Means within a column followed by the same letter are not significantly different (Student-Newman-Keuls test) at $P = 0.05$.

Mortality for the second trial was recorded for 47 days. Mean percent mortality for each treatment at 1, 2, 8, 29 and 47 days after exposure were selected to be representative of the exposure time course and are given in Table IV.

The ND4+Thiamethoxam treatment had the highest mean mortality and yielded significantly greater mortality than all other treatments for the entire testing period. At one day after exposure, only the ND4+Thiamethoxam treatment (10%) was significantly greater than any of the controls. Two days after exposure, in addition to ND4+Thiamethoxam treatment (20%), only Imidacloprid (10%) was significantly greater than controls. This same trend is seen in Table III until day 29 when Imidacloprid instant granules (62%) exceeded Imidacloprid (60%). Except for indoxacarb in honey (37%), the remaining treatments were not significantly greater than any of the controls. By day 47 when the trial was concluded, the ND4+Thiamethoxam treatment had the highest percent mortality at 100%, which was significantly greater than Imidacloprid instant granules (84%) and Imidacloprid (82%). Of the remaining treatments by day 47 only indoxacarb in honey (52%) was significantly greater than any of the controls.

TABLE IV

Mean % mortality (+/SD) of *T. albipes* adults after 1, 2, 8, 29, and 47 days exposure to 15 treatments in a non-forced bioassay.

| | Days | | | | |
|---|---|---|---|---|---|
| | 1 | 2 | 8 | 29 | 47 |
| Treatment | | | | | |
| ND4 + Thiamethoxam | 9.57 ± 5.59a | 19.93 ± 5.03a | 62.45 ± 10.79a | 97.81 ± 3.36a | 99.91 ± 0.21a |
| Over-the-counter | 4.48 ± 2.56b | 7.62 ± 3.94bc | 13.66 ± 5.85bc | 23.35 ± 7.70cde | 32.78 ± 8.25de |
| Imidacloprid (Exempt) | 4.16 ± 2.83bc | 10.41 ± 9.31b | 21.58 ± 11.63b | 60.48 ± 15.40b | 81.65 ± 13.18b |
| Maxforce Ant Gel | 2.99 ± 1.67bcd | 4.91 ± 0.98bc | 7.60 ± 1.84bc | 18.77 ± 4.44de | 32.95 ± 10.48de |
| DPX in Honey | 2.93 ± 1.98bcd | 5.59 ± 3.16bc | 12.31 ± 6.13bc | 37.22 ± 7.03c | 52.03 ± 8.26c |
| Termidor | 2.90 ± 2.45bcd | 4.10 ± 2.80c | 8.01 ± 4.44bc | 20.69 ± 5.67de | 32.01 ± 7.16de |
| DPX surface | 2.19 ± 2.42bcd | 2.56 ± 2.51c | 5.61 ± 4.96c | 16.59 ± 12.72de | 27.87 ± 14.59e |
| Control Maxforce Gel blank | 1.97 ± 1.98bcd | 2.75 ± 2.63c | 5.95 ± 5.57c | 16.90 ± 8.80de | 30.24 ± 6.79de |
| Control surface | 1.62 ± 0.62bcd | 2.10 ± 0.94c | 4.95 ± 2.38c | 16.10 ± 5.15de | 29.38 ± 4.94de |
| Demand CS | 1.40 ± 1.01bcd | 1.95 ± 1.16c | 4.27 ± 2.18c | 14.44 ± 7.97de | 24.69 ± 8.19e |
| DeltaDust | 1.22 ± 1.01bcd | 1.48 ± 1.29c | 3.81 ± 2.29c | 10.53 ± 5.01e | 20.64 ± 5.08e |
| XR007 | 0.98 ± 0.70bcd | 1.35 ± 0.91c | 4.72 ± 2.47c | 14.72 ± 5.14de | 29.68 ± 5.85de |
| Whitmire Ant Bait | 0.65 ± 1.28cd | 2.03 ± 3.78c | 15.00 ± 16.92bc | 32.71 ± 19.08cd | 47.11 ± 20.19cd |

TABLE IV-continued

Mean % mortality (+/SD) of *T. albipes* adults after 1, 2, 8, 29, and 47 days exposure to 15 treatments in a non-forced bioassay.

|  | Days | | | | |
|---|---|---|---|---|---|
|  | 1 | 2 | 8 | 29 | 47 |
| Control bait | 0.30 ± 0.31d | 1.07 ± 1.23c | 3.18 ± 2.93c | 10.67 ± 6.17e | 20.41 ± 6.50e |
| Imidacloprid Instant Gran.** | — | 1.63 ± 1.15c | 14.11 ± 8.66bc | 61.97 ± 16.01b | 84.46 ± 6.73b |
| Treatment Effects Statistics | | | | | |
| F | 8.90 | 10.30 | 20.72 | 31.94 | 34.93 |
| df | 14, 75 | 14, 75 | 14, 75 | 14, 75 | 14, 75 |
| P | 0.0001 | 0.0001 | 0.0001 | 0.0001 | 0.0001 |

[a]Means of 5 replicates, mean = 340.87, SD = 86.48. Means within a column followed by the same letter are not significantly different (Student-Newman-Keuls test) at $P = 0.05$.
**Non-randomized treatment initiated 1 day after other treatments.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An insect bait comprising:
   (a) a plurality of free amino acids in a concentration range of 2–7 g/100 ml of insect bait wherein one of the amino acids is asparagine in the concentration range of 1–5 g/100 ml of insect bait;
   (b) a sugar; and
   (c) a preservative.

2. The insect bait of claim 1, wherein the sugar is at least one selected from the group consisting of sucrose, fructose, glucose, maltose, trehalose, honey, cane syrup and molasses.

3. The insect bait of claim 2, wherein the sugar is sucrose.

4. The insect bait of claim 2, wherein the sugar has a concentration of about 20–60 g/100 ml of insect bait.

5. The insect bait of claim 1, wherein the preservative is at least one selected from the group consisting of sodium benzoate, citric acid, disodium octaborate tetrahydrate, and a mixture of sodium benzoate and citric acid.

6. An insect bait comprising:
   (a) a plurality of free amino acids in a concentration of about 2–7 g/100 ml of insect bait, wherein one of the amino acids is asparagine in the concentration range of 1–5 g/100 ml of insect bait; and
   (b) a sugar.

7. The insect bait of claim 6, wherein the sugar is at least one selected from the group consisting of sucrose, fructose, glucose, maltose, trehalose, honey, cane syrup and molasses.

8. The insect bait of claim 7, wherein the sugar is sucrose.

9. The insect bait of claim 7, wherein the sugar has a concentration of about 20–60 g/100 ml of insect bait.

* * * * *